United States Patent [19]

Giampapa

[11] Patent Number: 5,443,508
[45] Date of Patent: * Aug. 22, 1995

[54] SUBCUTANEOUS IMPLANTABLE MULTIPLE AGENT DELIVERY SYSTEM

[76] Inventor: Vincent C. Giampapa, 89 Valley Rd., Montclair, N.J. 07042

[ * ] Notice: The portion of the term of this patent subsequent to Apr. 13, 2010 has been disclaimed.

[21] Appl. No.: 151,377

[22] Filed: Nov. 12, 1993

Related U.S. Application Data

[63] Continuation-in-part of Ser. No. 24,426, Mar. 1, 1993, Pat. No. 5,391,164.

[51] Int. Cl.$^6$ ............................ A61F 2/02; A61K 9/22
[52] U.S. Cl. .................... 623/11; 604/891.1; 424/424; 424/425
[58] Field of Search ............... 604/890.1, 891.1, 892.1; 424/424, 425; 623/11

[56] References Cited

U.S. PATENT DOCUMENTS 5,201,728  4/1993  Giampapa ..................... 604/891.1

Primary Examiner—David Isabella
Assistant Examiner—Debra S. Brittingham
Attorney, Agent, or Firm—M. K. Silverman

[57] ABSTRACT

An implantable multiple-agent biologic delivery system includes a pod proportioned for subcutaneous implantation beneath the dermis of the skin, the pod including a porous surface and having at least one internal chamber which is in fluid communication with the porous surface. The system includes a dome proportioned for selectable detachable securement to the chamber of the pod. The dome includes interior chambers, each in fluid communication with the interior of the pod. Bio-acting agents, such as hormones, enzymes, biologic response modifiers, free radical scavengers, and other genetically altered cell cultures may be provided, within the chambers of the dome, prior to implantation. Such agents within the dome will, through the use of time release micropumps, enter the interior chambers of the pod for transmission, through the porous surfaces into a growth factor stimulated capillary matrix and then to the bloodstream of the user. The pod may be removed, refilled, and resecured to the dome upon exhaustion of its contents or upon medical requirement for changes in medication, or may be percutaneously refilled in situ through injection into the dome. The surface of the pod may be treated with one or more vascular growth factors or related biologic molecules.

14 Claims, 5 Drawing Sheets

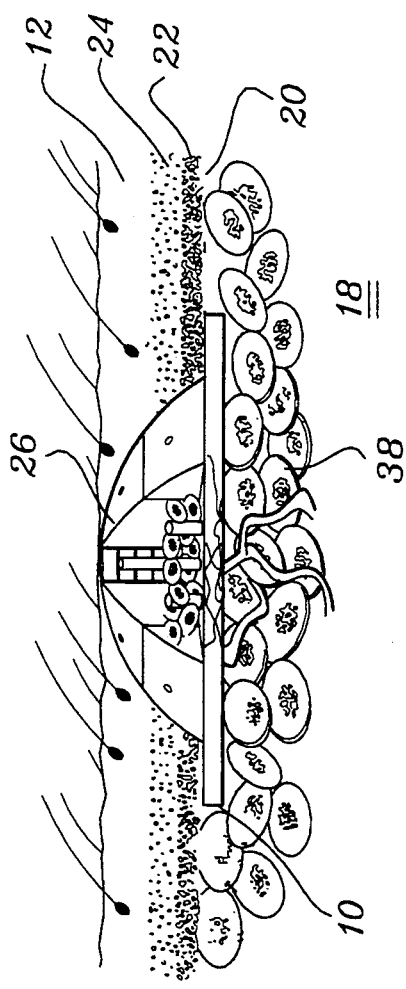
FIG. 1.
FIG. 2.
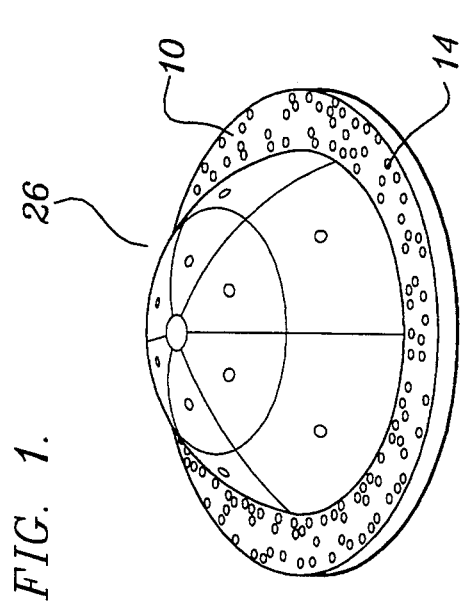
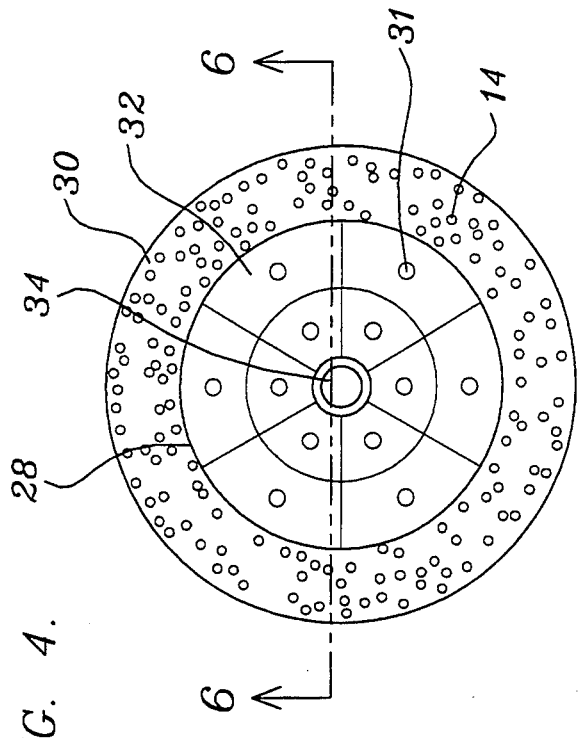
FIG. 3.
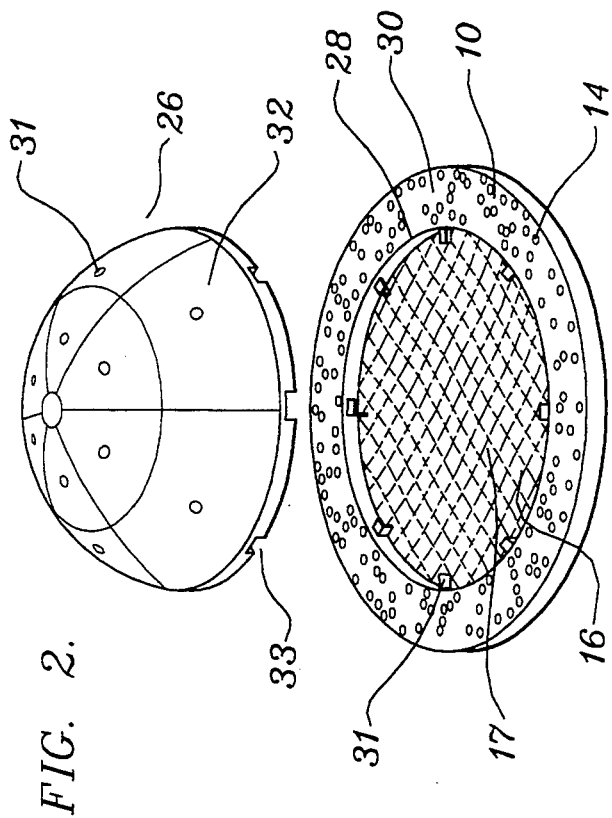
FIG. 4.

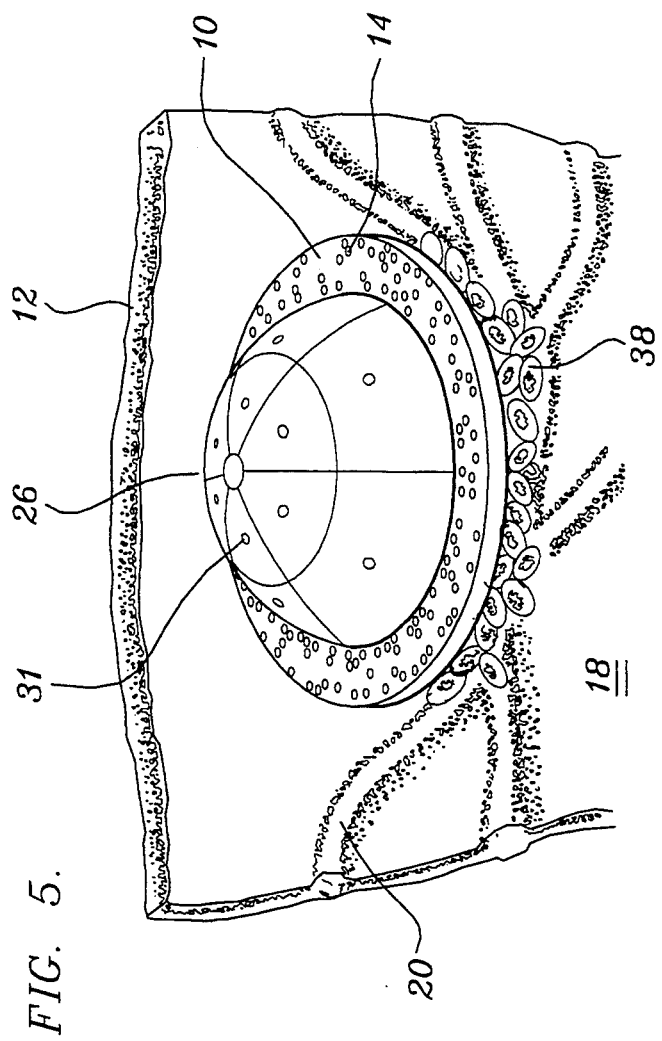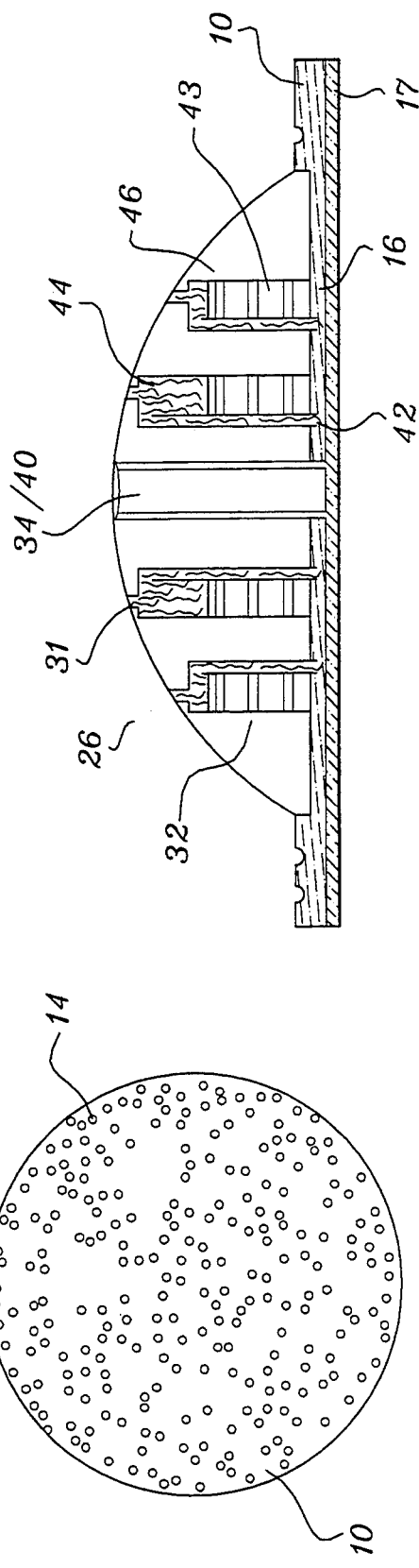

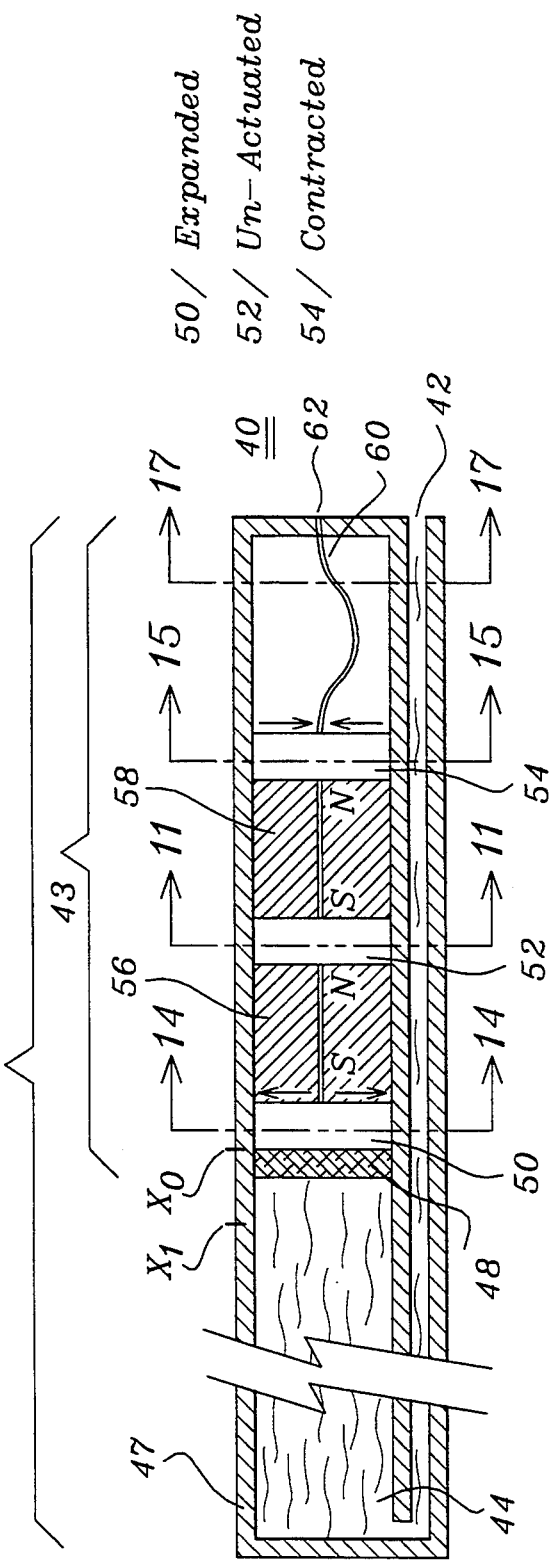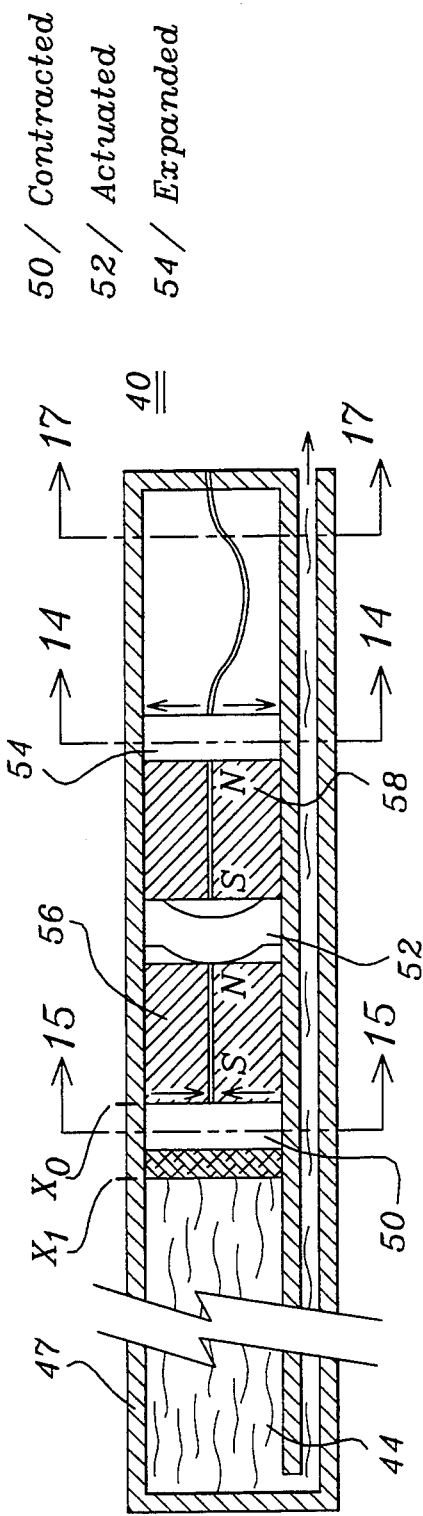

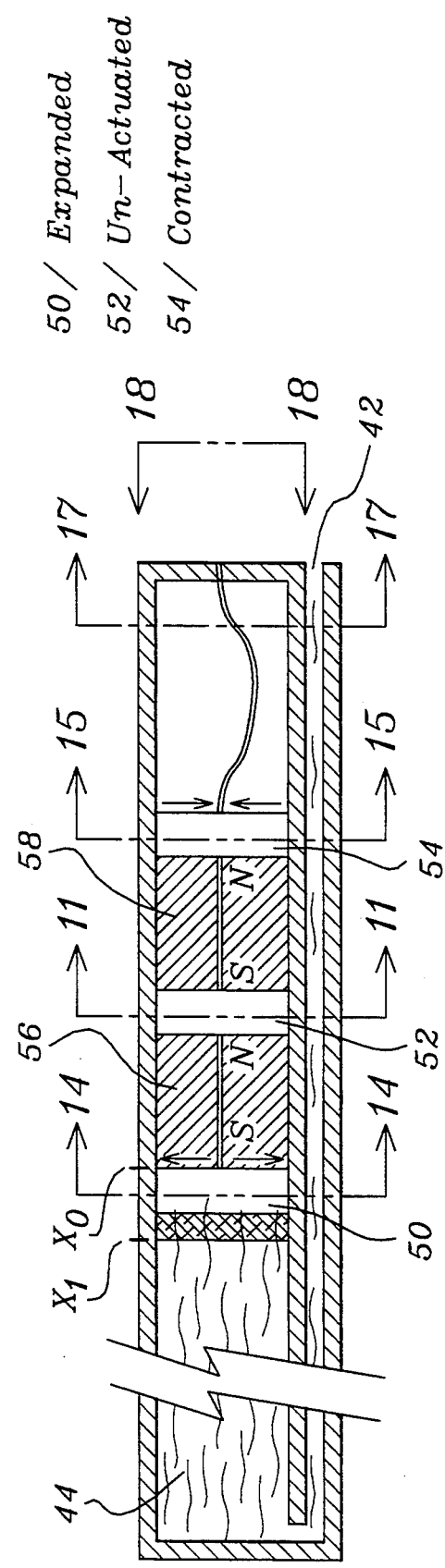
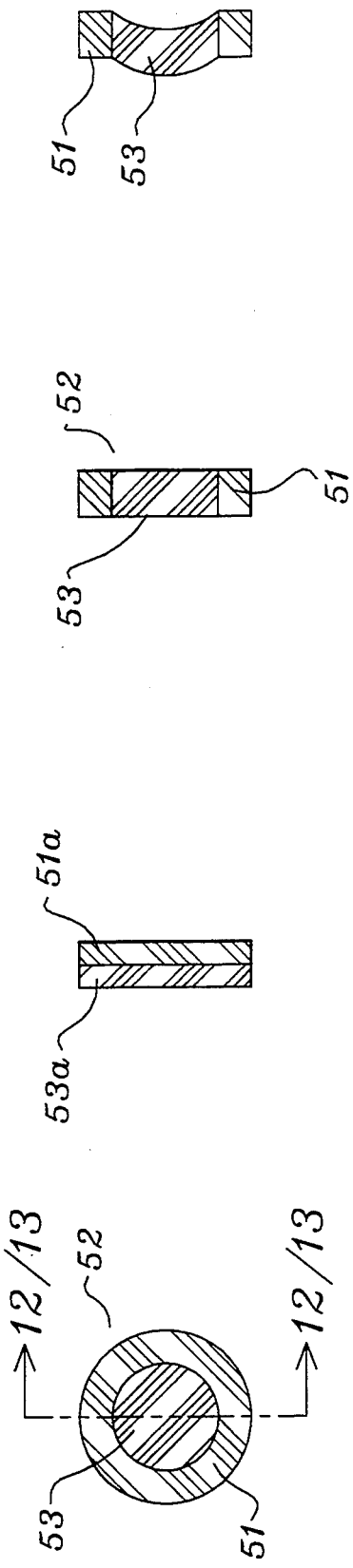

SUBCUTANEOUS IMPLANTABLE MULTIPLE AGENT DELIVERY SYSTEM

REFERENCE TO RELATED APPLICATION

This case is continuation-in-part of U.S. application Ser. No. 08/024426 filed Mar. 1, 1993, now U.S. Pat. No. 5,391,164.

BACKGROUND OF THE INVENTION

The present invention relates to the field of implantable vascular prosthetic devices, and more particularly, to a subcutaneous implant for integration into the vascular/capillary system of a patient for purposes of selectable dispensing, over an extended period of time, of pharmacologic and other bio-acting agents.

A problem which has developed in contemporary pharmacology and areas of bioengineering is that many bio-acting molecules resultant from such efforts are of a size, length, weight and complexity such that they are subject to attack by the enzymatic processes within the digestive tract when such drugs or bio-engineered agents are taken externally (orally). Further, the state-of-the-art of encapsulation and matrixing of drugs to minimize the effect of digestive tract acids, and to extend the release period thereof, are generally, limited to a number of hours in the resultant effective time period of release of such agents.

Recognizing the above limitations of orally delivered bio-acting agents, and realizing the limitations of drug delivery by means of hypodermic injection, a number of approaches, by way of implantable micro-infusion pumps/dispensers have appeared in the art. More particularly, such micro-pump and micro-dispensing systems have included electro-chemical means, piezo-electric means, osmotic means, of both an active and passive nature, and miniaturized classical electro-mechanical delivery means. All of these technologies have, as their goal, the provision of extended time-release of drugs and other bio-active substances directly into the bloodstream of the patient. For example, U.S. Pat. Nos. 4,886,514 and 4,902,278 to Maget relate to an implantable, electrochemically driven drug dispenser capable of achieving dispensing rates in the range of 0.01 ml per hour to as low as 0.001 ml (one microliter) per hour.

Implantable piezo-electric systems, intended for long-term dispensing of bio-acting agents are represented by U.S. Pat. Nos. 4,938,742 to Smits and 4,944,659 to Labbe. These technologies are entirely solid state and, therefore, are, in principle, capable of unlimited miniaturization and to control thereof by purely electronic means. Thereby, long term, low quantity delivery systems should be achievable by such means.

The category of so-called active osmotic pumps is represented by U.S. Pat. No. 4,898,582 to Faste and No. 5,030,216 to Theeuwes which employees chemo-mechanical processes which do not require any source of electrical energy such as a battery. In this technology, a membrane is reciprocated responsive to a chemical reaction to, over extended periods of time, provide controlled, long-term release of bio-acting substances.

So-called passive osmotic pump systems have appeared for use in both oral systems and have been suggested for subcutaneous delivery systems. Such pumps, which involve the use of lipids, are represented by U.S. Pat. Nos. 4,111,201 to Theeuwes; No. 4,439,196 to Higuchi; and No. 4,685,918 to Amidon et al. Passive osmotic pumps make use of a rigid enclosure having an expandable compartment which supplies pressure against an adjacent second compartment to effect a pressure gradient against the wall of the second compartment so that, over prolonged period of time, a bioacting agent within the second compartment will be forced across an aperture in the rigid enclosure and into the bloodstream or tissue of the patient. Such systems of osmotic delivery address drug delivery rates of picoliters per hour, that is, billionths of liters per hour. Accordingly, extremely low quantity and prolonged delivery rates are apparently achievable through the use of such osmotic systems. Nonetheless, these approaches do not address the needs of the patient or user having, as is often the case, the requirement for a timed, sequenced and/or pulsed delivery of a number of different bio-acting agents (often known as biologic response modifiers). Also, little is known regarding the long term effect of osmotic systems, when such systems are used in sub-cutaneous implants, as opposed to an orally-taken capsule.

A further concern in the area of implantable delivery systems is the ability of the vascular system to provide sufficient volume, rate, and pressure of blood flow to the delivery means to enable the bio-acting agents to enter the bloodstream on a reliable basis. Two approaches to this problem have appeared in the art. One is the approach of Powell (see U.S. Pat. No. 4,929,442) of providing an improved physiological carder to permit the particular bio-acting agent to become more effectively transferred to the bloodstream. A second approach to the problem of access to the vascular system is reflected in U.S. Pat. No. 4,820,626 (1989) to Williams et al, which is concerned with methods of treating the surface of subcutaneous implants with microvascular endothelial cells to better integrate the implant into the vascular system of the patient to achieve better bloodflow to the dispensed agents.

The instant invention is an improvement of the said technology of Williams in that use is made of one or a combination of so-called vascular growth factors which communicate directly with the so-called angiogenesis gene which, it is believed, is the basis of all human vascular development. Accordingly, through the use of growth factors and related biological molecules which have been recently discovered, vascular growth of capillaries, veins, and the like into the surface of an implant can be stimulated. This has been demonstrated by Ogawa, and others, who have placed vascular growth factor within a passive osmotic pump capsule, subcutaneously implanted the same, to thereby stimulate the growth of capillaries and related vascular structures which are identified with vascular growth and development.

Also there has appeared in the art such materials as polytetrafluoroethylene having specially configured fibers, fibrils and other structures adapted for vascular implantation. Accordingly, a combination of synthetic and organic materials have appeared in recent years which, in one fashion or another, stimulate vascular growth and/or activity.

The instant invention builds upon the above advances in molecular biology, material science and microelectronics. It more particularly provides for a selectably detachable component of a dispensing system in which a permanently implanted vascular portion of the system cooperates with a replaceable component thereof within which various biologic response modifiers, and other agents may be provided and dispensed at low rates, or pulsed, over prolonged periods into the implanted vascular portion and therefrom into the human body.

SUMMARY OF THE INVENTION

There is provided an implantable multiple-agent delivery system which includes a pod proportioned for subcutaneous implantation beneath the dermis of the skin, said pod comprising a porous surface and having at least one internal chamber therewithin which is in fluid communication with said porous surface. The system further includes a dome proportioned for complemental, selectable detachable securement upon said pod, the dome comprising a plurality of interior chambers, each having fluid communication with said internal chambers of said pod. Bio-acting agents such as hormones, enzymes, biologic response modifiers, free radical scavengers, genetically altered cell cultures and other therapeutic agents may be provided, within the chambers of said dome, prior to implantation. Each of said chambers will, through the use of time release means, enter said interior chambers of said pod for release, through the porous surfaces thereof, into a the stimulated vascular matrix and into the bloodstream of the user. Said dome may be removed, refilled, and resecured to said dome upon exhaustion of its contents or upon medical requirement for changes in medication. Alternatively, the chambers of said dome may be refilled percutaneously in situ by injection through septums on the dome. The exterior surface of said pod is treated with one or more vascular growth factors or related biologic molecules.

It is accordingly an object of the present invention to provide a subcutaneous vascular implant for purposes of extended sequenced pulsed time release delivery of a plurality of bio-acting agents.

It is another object of the present invention to provide a vascular implant having a component thereof which may be selectably removed, refilled with medication, and resecured to a permanently implanted vascular portion of the system or, alternatively, that can percutaneously re-filled.

It is a further object of the present invention to provide a means in the nature of a prosthetic gland from which needed hormones, related agents and combinations thereof and can, over a prolonged period of time, be released into the bloodstream.

The above and yet other objects and advantages of the present invention will become apparent from the hereinafter set forth Detailed Description of the Invention, Brief Description of the Drawings, and Claims appended herewith.

BRIEF DESCRIPTION OF THE DRAWINGS

FIG. 1 is a perspective, schematic view of the inventive system prior to implantation.

FIG. 2 is an exploded view of the system.

FIG. 3 is a side conceptual view of the system after implantation.

FIG. 4 is a top plan view of the system showing the septums in the dome.

FIG. 5 is a perspective conceptual view of the system implanted within the dermis.

FIG. 6 is a cross-sectional taken along Line 6—6 of FIG. 4, showing the agent delivery means including micropumps.

FIG. 7 is a bottom view of the inventive system.

FIG. 8, 9 an 10 are enlarged views of an individual agent delivery micropump, showing the sequence of operation thereof.

FIG. 11 is radial cross-sectional view taken along Line 11—11 of FIGS. 8 and 10.

FIG. 11a is a side view of an alternate embodiment of FIG. 11.

FIG. 12 is an axial cross-sectional view taken along Line 12—12 of FIG. 11.

FIG. 13 is a cross-sectional view taken along Line 13—13 of FIG. 11.

DETAILED DESCRIPTION OF THE INVENTION

Figure 16:
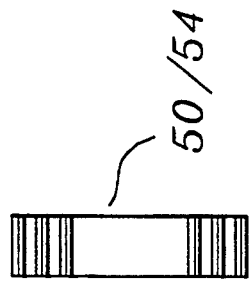
FIG. 16 is a cross-sectional view taken along Line 16—16 of FIG. 15.

With reference to FIGS. 1 to 7, the inventive system may be seen to include a pod 10 having a diameter preferably in the range of 1 to 3 centimeters. As such, it is proportioned for subcutaneous implantation beneath the epidermis 12 and dermis 22 (see FIG. 3). The surface of pod 10 contains a multiplicity of pores 14 and, as well, at least one internal chamber 16 which, through fluid transfer means 17 such as a capillary mesh or other permeable membrane, is in fluid communication with said pores 14. The walls of pod 10 are formed of a porous silicone or polytetrafloroethylene to permit ease of ingrowth of capillaries within tissue layer 18 and at subcutaneous border 20. See FIG. 3 and 5.

In a preferred embodiment, the porous surface of pod 10 is treated with one or more vascular growth factors, or related biologically active materials which operate to communicate directly with the anglogenesis genes of nearly cells which, it is believed, are responsible for all vascular development. Accordingly, growth factors and the like may be viewed as genetic "receivers" while the anglogenesis genes operate as genetic "transmitters". A number of vascular growth factors have been identified. These are vascular endothelial growth factor (VEGF), platelet derived growth factor (PDGF), vascular permeability growth factor (VPF), basic fibroblast growth factor (bFGF), and transforming growth factor beta (TGF-$\beta$). Related molecules which operate in a similar fashion may also be used. These are known cytokines and gangliosides.

The use of endothelial cells upon the surface of a prosthetic device, employed in the context of vascular surgery, is known as is taught in U.S. Pat. No. 4,820,626 (1989) to Williams et al entitled A Method of Treating a Synthetic or Naturally Occurring Surface with Microvascular Endothelial Cells. The instant invention, however, does not relate to the use of a growth factor treated surface in the context of a surgical device or system. Rather, said pod 10 operates as a permanently implanted component of a long term multi-agent drug delivery system. Its effectiveness is maximized by reason of its placement at the subcutaneous border 20 of the patient, this constituting the location of greatest blood flow. As such, it is an ideal location for any agent dispensing device which relies, for its efficacy, upon permanent access to a relatively consistent of level of blood flow. As may be noted in FIG. 3, the subcutaneous border 20 is defined by the interface between dermis 22 and tissue layer 18. Between dermis 22 and epidermis 12 is the dermal layer known as stratum germinativium 24.

It is established in the literature that capillary growth may be artificially generated through the implantation of vascular growth factors inside of an osmotic implant. See for example, Ogawa et al, "Transforming Growth Factors Beta One and Beta Two Induce Synthesis and Accumulation of Hyluronate and Chondroitin Sulfate In-Vivo", 3 Growth Factors 53–62 (1990). Further, the medical literature concerning growth factors contains over 200 papers on the subject of vascular growth factors published since 1989. Accordingly, the technology of the use of vascular growth factors to stimulate capillary growth is known in the art.

The present drug delivery system further includes a dome 26 (See FIGS. 1 to 6) which is proportioned for complemental, detachable securement on top of pod 10 and, more particularly, within the inner circumference 28 of annular region 30 of the pod 10. Said dome 26 and pod 10 may be secured through the use of bayonet lock elements 31 and 33 of the type shown in the exploded view of FIG. 2.

As may be noted in the top view of FIG. 4, and the radial cross-sectional view of FIG. 6, the interior of dome 26 comprises a plurality of interior chambers 32 each having fluid communication with fluid transfer means 17 of said interior chamber 16 of pod 10. Also shown in FIG. 6 is axial region 34 within which control electronics and battery 40 are placed.

As may be noted in the view of FIG. 3, the top of dome 26 will reach through dermis 22 and will stop at epidermis layer 12.

In another embodiment, the top of dome 26 may protrude above epidermis 12 in the manner taught in U.S. Pat. No. 4,552,561 (1985) to Eckenhoff, entitled Body Mount Pump which teaches the use of an implantable pump having a transparent top through which the contents of the dome portion may be seen.

In either embodiment, an essential concept to the instant invention is that a plurality of bio-acting agents are placed within respective chambers 32 of dome 26 and, after their exhaustion, or upon the election of the physician, dome 26 is, through minor out-patient surgery, be removed from pod 10, refilled, and then re-secured to pod 10. Alternatively, each reservoir 44, described below, may be re-filled in situ percutaneously through septums 31.

One fascinating embodiment of the present system is that of hybrid organ or gland. Genetically altered encapsulated cell cultures contained within the chambers 32 of the dome 26 would be protected by the permeable membrane of fluid transfer means 17 from attack by antibodies, cells, and other elements of the body's immune system, but would be able to produce the desired biological substances for the host patient, releasing them through the neovascular network 38.

This particular embodiment of the system has several advantages over passive osmotic systems as, for example, is reflected in U.S. Pat. No. 5,030,216 (1991) to Theeuwes, entitled Osmotically Driven Syringe. There would be minimal need for an internal micropump system or biological sensors to control drug dispensing, as the cell cultures would, organically, constantly monitor levels of particular agents in the host bloodstream and produce the necessary agents as required. The permeable membrane 17, while protecting the cell cultures from the body's immune system, would permit nutrients and oxygen to pass through, nourishing these cells and allowing them to secrete the desired therapeutic substances, which would lessen or eliminate the need to replace the cell cultures by surgical removal of the dome or by re-filling it in situ percutaneously through septums 31. Finally, any accidental rupture of the dome would likely result only in destruction of the resident cell culture by the patient's immune system, with none of the possibly dangerous reactions conceivable if a reservoir rupture were to result in a drug overdose.

While the hybrid organ/gland embodiment of the instant system is presently theoretical, researchers have been exploring the use of other encapsulated cell technologies in the treatment of chronic disorders for some time, and the commercialization of these technologies has begun, led by companies such as BioHybrid Technologies of Shrewsbury, Massachusetts, and Cytotheraputics, Inc. of Providence, R.I., which recently announced the initiation of an FDA-approved Phase I human clinical trial utilizing polymer-encapsulated islets of langerhans to be implanted into both Type I (insulin-dependent) and Type II (adult-onset) diabetic patients.

Potential technologies for effecting extended duration time release run the gamut from substantially passive means such as osmotic pumps to electrochemically driven drug dispensing means (see Maget, discussed in the Background of the Invention), to systems requiting use of a battery acting as a source of low level power, to a piezoelectric micro pump and microvalves, such valves operating within chambers 32 of dome 26, as is generally taught in the references to Smits and Labbe, discussed in the Background of the Invention. Such solid state piezo-electric means are particularly suitable where small rates of release, e.g., nanoliters per hour, over a period of months, are required.

An adaptation of Smits and Labbe that is particularly suitable to use within the instant system is shown in the views of FIGS. 8 through 18. More particularly there is, as above noted, shown in FIG. 6 a plurality of annular chambers 32 each containing a micro-pump 46 consisting of micromechanical means 43 and said biologic agent reservoir 44. The same are shown in enlarged view in FIGS. 8, 9 and 10, as is the outlet port 42 by which fluid interface is achieved between reservoir 44 and fluid transfer means 17 of pod 10. The micromechanical means 43 may be seen to include a biologic material barrier 48, first radially expansive piezo-electric means 50, axially expansive piezo-electric means 52, and second radially expansive piezo-electric means 54. These elements are shown in radial view FIGS. 11, 14 and 15 and in side view in FIGS. 12, 13 and 16.

Figure 15:
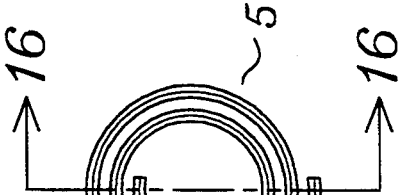
FIG. 15 is a radial cross-sectional view taken along Line 15—15 of FIGS. 8, 9 and 10.
Figure 14:
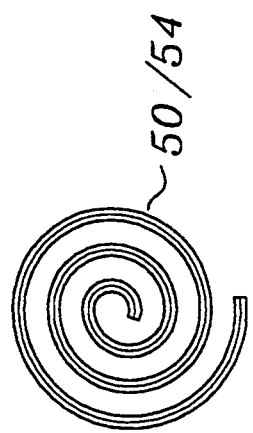
FIG. 14 is a radial cross-sectional view taken along Line 14—14 of FIGS. 8, 9 and 10.
Figure 18:
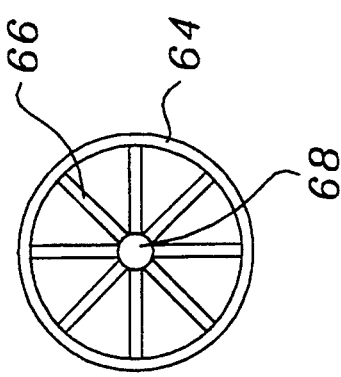
FIG. 18 is a fight end view of FIGS. 8, 9 and 10.
Figure 17:
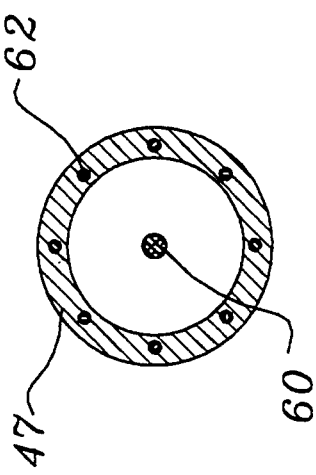
FIG. 17 is a radial cross-sectional view taken along Line 17—17 of FIGS. 8, 9 and 10.

The fundamental property of piezo-electric elements is that they will change in geometry as a function of changes in electrical current applied to the constituent elements thereof. More particularly, the piezo-electric elements employed in the present embodiment of the invention each consists of two elements which are in electro-thermal communication with each other. More particularly, the radially expansive elements shown in FIGS. 14 and 15 consist of strips of metallic materials having different electrothermal properties. Accordingly, such piezo-electric elements are typically referred to as bimetallic elements. As a consequence of different co-efficient of expansion of these elements in response to a given level of electric current, one of such bimetallic elements will expand more rapidly than the other. Consequently, dependent upon the amount of current applied to either or both of such bimetallic elements, the degree of expansion (FIG. 14) or contraction (FIG. 15) may be controlled. This may be more particularly seen with reference to FIG. 8 in which element 50 is employed in its expanded state (see FIG. 14) while element 54 is employed in its contracted state (see FIG. 15). The use of the radially expanded state of the spiral element of FIG. 15 is employed when an anchoring function relative to the interior surface of wall 47 of the microelectronic means 43 is necessary. This would typically be the case during the standby mode shown in FIG. 8 in that, in the standby mode, one does not wish to eject any fluid from reservoir 44 through outlet 42. Therefore element 14 will be the expanded state while element 54 is in its contractive state. It is noted that wire 60, also shown in FIGS. 8 to 10, outputs through rear end wall 52 to elements 64 and 66 of the input shown in FIG. 18, while contact 68 communicates with battery 40 and pump control inputs 62 that are in electronic communication with control buss 64 which communicates with said system control means 34. See FIGS. 10, 17 and 18.

Between said radially expandable elements 50 and 54 is axially expandable element 52 shown in radial and axial view in FIGS. 11 through 13. Said element consists of a first bimetallic element 51 and second bimetallic element 53, each having different coefficients of expansion responsive to a given current. When no current is present, the condition shown in FIGS. 11 and 12 exists. Upon application of an appropriate current, radial expansion of the inner element 53 will occur thereby giving rise to a buckling effect shown in FIG. 13. This buckling effect (see also FIG. 9) results in the application of pressure against pole magnet 56. This makes possible the advance of element 50 from position $X_0$ to $X_1$ which is illustrated in FIG. 9. Concurrently with such radial expansion of element 52, element 54 will expand as is shown at right hand side of FIG. 9 thereby providing an anchoring effect relative to wall 47. This anchoring effect is necessary to maintain pole magnet 58 in the position shown in FIG. 9.

After the advance of the first piezo-electric element 50 from position $X_0$ to $X_1$ has occurred and with it biologic barrier 48, element 52 is permitted to return to its "unbuckled" condition, as shown in FIG. 10. Accordingly, the view of FIG. 10, showing a second standby mode, is the same as FIG. 8, except that the entire assembly of elements 48, 50 56, 52, 58 and 54 has been advanced to the left from position $X_0$ to $X_1$ and, with it a predetermined number of nanoliters of solution of biologic agent from reservoir 44 has exited port 542 into fluid transfer means 17. The role of pole magnets 56 and 58 is to assure that elements 52 and 54 will be advanced to the left by the same distance that element 50 has bee so advanced.

When it becomes necessary to again discharge a particular quantity of solution from reservoir 44, current is again applied, through wire 60, to the system such that the operational step shown in FIG. 9 may be repeated. Accordingly, through the use of such solid state micromechanical piezo-electric and mechanical means, extremely small rates of release, as low as nanoliter per month, may be affected. When release of larger quantities is required, several of the "forward steps" shown in the State 2 operational mode of FIG. 9 may be accomplished in rapid succession of each other.

The instant invention may also be practiced through the use of relatively crude subcutaneous implant devices such as that reflected in U.S. Pat. No. 3,443,561 (1960) Reed, entitled Subcutaneous Implant Device, previously used in veterinary applications, as the pod 10 of the present system. Accordingly, long known implants of the type of Reed may be equipped with a dome, as above described, to thereby provide for an extended time release capability of a plurality of a bioacting agents.

In broad concept the instant invention may be viewed as a prosthetic gland in that, through its operation, a sustained release of hormones of various types, including, human growth factors designed to increase muscle mass, decrease body fat deposition, and stimulate immunological responses, may be employed. More generally, such hormones are known as biologic response modifiers and, generally relate to those classes of agents which have been determined to be associated with the aging process or immune system. More particularly, the absence or decrease of hormones and/or their growth factors as well as free radical scavengers have been identified as a primary cause of the aging process. To use the above transmitter/receiver analogy, the operation of the human gene may be compared to that of a transmitter, while the operation of growth factors and related molecules may be viewed as genetic receivers or receptors. In other words, the aging process is now believed to be the result of a failure in one or more of the genetic processes of transmission and reception of genetic information. The avenues by which genetic instructions travel from genes to growth factors is often termed the enzymatic pathways. More particularly, certain enzymes are associated with the operation of so-called messenger DNA which communicates genetic instructions from the gene to the growth factor where the instructions of the gene are then executed in the particular tissue with which that growth factor is associated. Growth factors or hormone regulated processes which affect of an enzymatic pathway may be purely local to the cell (an autocrine pathway) or the genetic instruction may be delivered at a considerable biological distance (an endocrine pathway).

In that genetic research has, as yet, been unable to locate any so-called aging gene, it is believed that most manifestations of the aging process occur as a result of breakdown in either or both the enzymatic pathways and/or of the actual growth factors which to execute the genetic instructions. More particularly, in vitro experiments have shown that most genes have the capability of reproducing tens of thousands of times, this corresponding to what would relate to dozens of normal lifespan specie generations. It is therefore now believed, that most aspects of aging are a result of the inability of cell classes within tissues to continue to execute genetic instructions, that is, it is now widely believed that aging, as it is presently understood, is primarily a result of the failure of cells to carry out essential genetic instructions from genes which, in and of themselves, appear to be capable of functioning indefinitely.

As a more modest goal of what has become known as growth factor therapy, certain diseases which cause a more dramatic manifestations of the aging process can, through the system of the present invention, be directly treated. For example, osteoporosis which is directly related to growth hormone deficiency can be treated; similarly, certain areas of the skin and related fat deposits which are generally associated with aging, may be treated through the use of epidermal growth factors which have been identified including the above mentioned fibroblast growth factor (bFGF) which is generally associated with the growth of muscle mass.

Further, one popular theory of aging is the process known as glycolysolation in which certain compounds causes a cross linking of proteins thereby rendering the above referred to enzymatic pathways less efficient. Accordingly, through the use of hormones and other molecules, such as free radical scavengers, such cross-linking or glycolysolation of proteins necessary for healthy enzymatic pathways, can be effectively eliminated.

The important role of growth factors in combating diseases, such as carcinomas and anti-viral diseases, is recognized by Powell, in U.S. Pat. No. 4,929,442 (1990) (see Background of the Invention). He discusses the importance of glycoproteins and growth factors in the combating of certain topical and subcutaneous conditions. Further, Powell teaches a physiologically acceptable carrier which in the instant invention and, more particularly, within the chambers of dome 26, may be employed to increase the effectiveness of other bio-acting agents which may be employed within the scope of the present invention. Further, through the use of vascular growth factors in at least one of the chambers 32 of dome 26, the vascular growth factor applied to pores 14 at the surface of pod 10 will co-act to provide long term "nourishment" to the vascular growth factors applied to the surface of pod 10 and to the artificially created capillary growth (see FIG. 5) within tissue 18.

Persons suffering from high cholesterol may be effectively treated through the use of Lovastatin and other anti-cholesterol drugs which are more effective when delivered in small quantities over an extended period of time. Further, even persons having a normal cholesterol level can benefit from the use of such anti-cholesterol agents to decrease age related arterial damage as well as to provide improved oxygenation to the entire central nervous system as well as to other vital organs. Accordingly, within the scope of the present invention, it is anticipated that persons not considered ill by earlier medical standards, will be able to make advantageous use of the instant system.

Further, there exists numerous medical therapies in which one drug or drag system is optimally employed in combination with a second or many other drugs such that a desired synergistic effect can be achieved. For example, U.S. Pat. No. 4,971,951 (1990) to Garcia y Bellon et al, teaches a therapy known as Insulin Potentiation Therapy which has application to numerous diseases. In the practice of Insulin Potentiation Therapy the effect of the particular therapeutic or bio-acting agent is potentiated by the parental injection to the patient, approximately 20 minutes prior to the administration of the therapeutic agent, of a prescribed dosage of insulin. In other words, the action of the therapeutic or bio-acting agent of interest is potentiated, within the intracellular compartment, that is, the permeability to cross the cell membrane is enhanced, by a "pulse" of insulin at a prescribed time prior to the administration of the therapeutic agent, (which in the case of insulin potentiation therapy involves the combination of glucose or dextrose with the therapeutic agent) must occur. As such, the present system will be particularly useful in that one compartment 32 within dome 26 may contain a material such as insulin which, through the use of electronic means as is taught in the references to Smits supra and others, may be pulsed into the subcutaneous border 20 at a programmed time prior to pulsing from one or more other compartments of dome 26.

More generally, through the instant invention, a physician such as endocrinologist may prescribe a number of hormonal, enzymatic or genetic therapies having a variety of different volumetric, molaric and time release specifications. Further, the external surface of pod 10 may be equipped with any of a variety of biological sensors such that the electrical, chemical or mechanical pump means (as the case may be) are initiated in response to particular indications which are monitored through blood flow in tissue 18 within the region of said artificially stimulated capillary ingrowth 38. It is noted that the present system in particular suitable for use with genetically altered cell cultures in that their storage within the micropumps 46 can protect the cultures from potential immunologic response, while the micropumps release components of such cell cultures not subject to such a potential response.

In lieu of micropumps 46, it is to be further appreciated that, within the scope of the present invention, compartments 32 of dome 26 may be provided with pre-packaged time release elements such as bio-acting materials contained within silicone tubules as are presently manufactured and sold by the Leiras Medical Corporation of Helsinki, Finland. A number of such implantable tubules now exist for the release of birth control acting hormones. However, such tubules may be equipped with other hormones, therapeutic agents and the like as above discussed, and the geometry thereof adapted for implantation within compartments 32 of the dome 26.

Accordingly, while there has been shown and described of the preferred embodiment of the present invention it is to be appreciated that the invention may be embodied otherwise than is here and specifically shown and described and, within said embodiment, certain changes may be made within the form and arrangement of the parts without departing of the underlying principles of this invention as set forth in the Claims appended herewith.

Having thus described my invention what I claim as new, useful and non-obvious and, accordingly, secured by Letters Pat. of the United States is:

1. A removable subcutaneously implantable, multiple-agent delivery system, comprising:
   (a) a pod for subcutaneous implantation beneath the dermis of the human body, said pod comprising a porous surface between an interior and exterior of a bottom thereof and further comprising fluid transfer means in fluid communication with said porous surface, said pod having an opening at a top thereof, said pod formed of a biocompatible material, the exterior of the bottom of said pod provided with one or more vascular growth factors to promote growth of blood capillaries into and about said porous surface;
   (b) a dome proportioned for detachable securement about said opening of said pod, said dome including at least one chamber having selectable fluid communication with said fluid transfer means of said pod, in which bio-acting materials may be stored within said chambers of said dome prior to implantation, said dome formed of a biocompatible material; and (c) programmable time dependent biological agent release means within said chambers of said dome and said fluid transfer means of said pod, whereby said agents are controllably released from said chamber of said dome and into said pod and, therefrom, through said porous surface into the bloodstream, in which said dome, after exhaustion of the agents there within, may be removed, refilled and resecured to said pod.

2. The system as recited in claim 1 in which said vascular growth factors are selected from the group of growth factors consisting essentially of vascular endothelial growth factor, platelet growth factor, vascular permeability factor, basic fibroblast growth factor and transforming growth factor beta.

3. The system as recited in claim 2 in which said pod is formed of a silastic material having a porous vascular ingrowth characteristic.

4. The system as recited in claim 2 in which said agent release means include piezo electric micropump means within said at least one chamber of said dome.

5. The system as recited in claim 1 in which said programmable time dependent agent release means comprise micromechanical and microelectronic means.

6. The system as recited in claim 5 in which said vascular growth factors are also contained within a compartment of said dome.

7. The system as recited in claim 5 in which said fluid transfer means comprise capillary means.

8. The system as recited on claim 7 in which said dome includes at least one septum by which at least one chamber in said dome can be re-filled in situ by percutaneous injection.

9. The system is recited in claim 8 in which control means for said agent release means are situated within an axial central core and in said dome.

10. The system as recited in claim 5 in which control means for said agent release means are situated within an axial central core in said dome.

11. The system as recited in claim 10 in which said vascular growth factors are selected from the group of growth factors consisting essentially of vascular endothelial growth factor, platelet growth factor, vascular permeability factor, basic fibroblast growth factor and transforming growth factor beta.

12. The system as recited in claim 1 in which said pod is formed of a silastic material having a porous vascular ingrowth characteristic.

13. The system as recited in claim 12 in which said silastic material is selected from the group consisting of silicone and plytetrafluorethylene.

14. The system as recited in claim 12 in which said fluid transfer means comprise capillary means.

* * * * *